United States Patent [19]

Chauvette

[11] 4,334,065
[45] Jun. 8, 1982

[54] CEPHALOSPORIN INTERMEDIATES

[75] Inventor: Robert R. Chauvette, Indianapolis, Ind.

[73] Assignee: Eli Lilly and Company, Indianapolis, Ind.

[21] Appl. No.: 209,440

[22] Filed: Nov. 24, 1980

[51] Int. Cl.³ .......................................... C07D 501/18
[52] U.S. Cl. ...................................... 544/30; 544/90; 260/239 A
[58] Field of Search ........................................ 544/30

[56] References Cited

U.S. PATENT DOCUMENTS 4,198,406  4/1980  Hardy et al. ........................ 544/27

OTHER PUBLICATIONS

J. Altman et al., "7-N-Amidinocephalosporins", *J. Med. Chem.*, 1975, vol. 18, No. 6, pp. 627–630.

F. J. Lund, "6β-Amidinopenicillanic Acids–Synthesis and Antibacterial Properties", Recent Advances in the Chemistry of β-Lactam Antibiotics, Ed. J. Elks, Specialist Publication Chemical Society, No. 28, 1977, pp. 25–45.

B. Baltzer et al., "Degradation of Mecillinam in Aqueous Solution", *J. Pharm. Soc.*, 68, No. 10, Oct., 1979, pp. 1207–1215.

*Primary Examiner*—Paul M. Coughlan, Jr.
*Attorney, Agent, or Firm*—William B. Scanlon; Arthur R. Whale

[57] ABSTRACT

7α-(Dimethylamidino)-3-cephem ester 1α-oxides represented by the formula

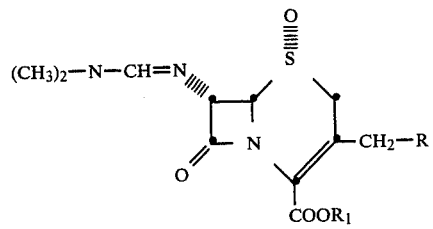

wherein R is hydrogen or acetoxy and $R_1$ is a carboxy protecting group, are prepared via DBU epimerization of the corresponding 7β-isomer. When R is hydrogen the intermediates are useful in the preparation of the 7β-acylamino-7α-methoxy-1-oxa-β-lactam antibiotics, and when R is acetoxy the compounds are intermediates to 7β-acylamino-7α-methoxy-3-exomethylenecepham compounds.

13 Claims, No Drawings

CEPHALOSPORIN INTERMEDIATES

SUMMARY OF THE INVENTION

This invention relates to cephalosporin compounds. In particular, this invention relates to 7-epi-dimethylamidino-3-cephem-4-carboxylic acid ester α-sulfoxides represented by the following structural formula 1.

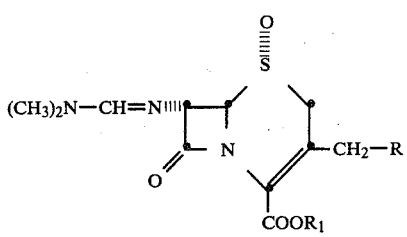

wherein R is hydrogen or acetoxy; $R_1$ is a carboxy protecting group; and the acid addition salts thereof.

In the above structural formula 1, the dotted bonding lines indicate the α-configuration. For example, the dimethylamidino group in the 7-position of the cephem ring system has the α-configuration and is thus situated behind the plane of the β-lactam ring in contrast to the natural or β-configuration of the cephalosporin antibiotics having the 7-position substituent located spacially above the plane of the β-lactam ring.

The compounds of the invention are basic compounds which form acid addition salts with suitable acids such as the mineral acids, hydrochloric acid, and sulfuric acid, as well as with the strong organic acids such as the organic sulfonic acids.

The compounds are prepared by reacting an ester of the appropriate cephalosporin nucleus with dimethylformamide dimethylacetal, or with dimethylformamide and phosphorus trichloride to form the corresponding 7β-dimethylaminomethyleneamino substituted nucleus ester. The latter is then reacted with a peracid to form the 7β-dimethylaminomethyleneamino substituted 1α-oxide. The latter sulfoxide is then reacted in the cold with 1,5-diazabicyclo[5.4.0]undec-5-ene (DBU) to effect epimerization at the 7-position and provide a compound of the invention.

The compounds of the invention represented by the formula 1 above wherein R is hydrogen are useful in the preparation of 1-oxa β-lactam antibiotics as described hereinafter. The compounds represented by the formula 1 wherein R is acetoxy are useful in the preparation of 7-acylamino-7-methoxycephalosporin antibiotics.

DETAILED DESCRIPTION OF THE INVENTION

The cephalosporin intermediate compounds of this invention represented by the above formula 1 are formally named as esters of 7α-[(dimethylaminomethyleneamine)amino]-3-methyl (or 3-acetoxymethyl)-3-cephem-4-carboxylic acid 1α-oxide. For convenience, the dimethylaminomethyleneamino substituent is referred to herein as the dimethylamidino group. The dimethylamidino group in the 7-position of the cephem nucleus has the unnatural or α-configuration which is epimeric to the natural or β-configuration of the cephalosporin antibiotics. For example, cephalosporin C obtained by fermentation of *Cephalosporium acremonium* has its side chain, the α-aminodipoyl group, in the β-configuration as do the semisynthetic antibiotics obtained from cephalosporin C via the nucleus 7-aminocephalosporanic acid. Also, as shown by the dotted bonded lines in formula 1, the compounds of the invention are sulfoxides wherein the sulfoxide bond has the α-configuration.

The compounds of the invention are prepared from the known cephalosporin nucleus compounds, 7-aminocephalosporanic acid (7-ACA) and 7-aminodesacetoxycephalosporanic acid (7-ADCA) in esterified form. The cephalosporin nuclei have the natural or β-configuration for the 7-amino group.

The compounds of the invention are obtained by first preparing a 7β-dimethylamidino nucleus ester. The dimethylamidino nucleus ester is then oxidized with a peracid to provide the 7β-dimethylamidino substituted nucleus ester 1α-oxide and the latter is epimerized to a compound of the invention, a 7α-dimethylamidino cephalosporin ester 1α-oxide. The 7β-dimethylamidino group is formed by reacting an ester of 7-aminocephalosporanic acid or 7-aminodesacetoxycephalosporanic acid in dry dimethylformamide with phosphorus trichloride. The reaction is carried out conveniently at room temperature although somewhat elevated temperatures can be used. The dimethylformamide is generally used in excess amount and is best employed as the solvent for the reaction. For each mole of 7-amino nucleus ester, approximately 2 moles of phosphorus trichloride are employed. The reaction is carried out under substantially anhydrous conditions and, accordingly, the dimethylformamide employed in the reaction is dried beforehand.

The reaction is generally complete in between about 12 and about 16 hours when carried out at room temperatures. The dimethylamidino ester is recovered from the reaction mixture as the free base in crystalline form as follows. The reaction mixture is poured into a mixture of a water immiscible organic solvent such as ethyl acetate and an aqueous basic solution, for example, an aqueous solution of sodium bicarbonate or carbonate. The aqueous basic solution is preferably saturated with sodium chloride to enhance the uptake of the basic product into the organic layer. The organic layer containing the dimethylamidino ester product is separated from the aqueous layer, washed, dried, and evaporated to dryness, preferably under reduced pressure. The residue of product crystallizes on standing and can be further purified by trituration with diethyl ether or pentane.

Alternatively, the 7β-dimethylamidino ester is prepared by reacting the 7-amino nucleus ester with an excess of dimethylformamide dimethylacetal. The reaction is carried out conveniently at room temperatures or at somewhat elevated temperatures and is generally complete in between about 12 to about 16 hours. The 7β-dimethylamidino ester is recovered as the free base in crystalline form by pouring the reaction mixture into a mixture of a water immiscible organic solvent such as ethyl acetate and ice water. The organic phase containing the product is separated, washed with brine, dried, and evaporated to dryness. The product is obtained crystalline by trituration with a solvent such as diethyl ether or petroleum ether.

The 7β-dimethylamidino ester is then oxidized to form the α-sulfoxide by reacting the ester with a peracid. Preferably, the reaction is carried out in an aqueous medium containing a water miscible organic solvent preferably acetone, acetonitrile or other suitable water miscible solvent such as dimethylacetamide at about room temperature. The oxidation proceeds rapidly and the sulfoxide formation is essentially complete in from about 1 to about 2 hours.

Peracids which can be used in the oxidation include those normally employed in the preparation of cephalosporin sulfoxides such as peracetic acid, perbenzoic acid, m-chloroperbenzoic acid, perphthalic acid, and like peracids. For each equivalent of the dimethylamidino ester, a slight excess of one equivalent of the peracid is employed. For example, when 1 mole of the dimethylamidino ester is employed, 1.1 mole of the peracid is suitable. Excess peracid can be employed, if desired; however, a large excess is to be avoided to prevent overoxidation to the sulfone.

The 7β-dimethylamidino ester 1α-oxide formed in the above-described oxidation is isolated from the reaction mixture by first concentrating the reaction mixture to remove the water immiscible volatile solvent, followed by extraction of the aqueous concentrate with a water immiscible organic solvent, such as ethyl acetate, to remove any excess peracid remaining in the aqueous phase. The aqueous phase is then slurried with ethyl acetate and the pH of the slurry is adjusted to a pH of about 7.5 with 1 N sodium hydroxide. The organic layer is separated, washed, dried, and concentrated under reduced pressure. In many instances, the 7β-dimethylamidino ester 1α-oxide crystallizes from the concentrate. When crystallization does not occur, the concentrate can be evaporated to dryness and the product obtained crystalline by trituration with a suitable solvent such as diethyl ether.

The 7β-dimethylamidino ester 1α-oxide is then epimerized to obtain the compounds of the invention. The process by which the epimerization is carried out is a further aspect of this invention. It has been found that the epimerization of the 7β-dimethylamidino ester 1α-oxides occurs rapidly at low temperatures to provide the desired epimer of the invention. According to the process of this invention, a 7β-dimethylamidino ester 1α-oxide represented by the following structural formula

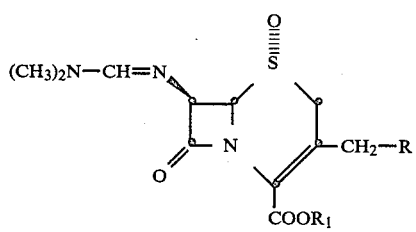

wherein R is hydrogen or acetoxy, and R$_1$ is a carboxy protecting group; is treated in an inert organic solvent at a temperature between about −10° C. and 25° C. with 1,5-diazabicyclo[5.4.0]undec-5-ene (DBU) to provide the 7α-dimethylamidino epimer represented by the structural formula 1.

The DBU is used in an amount corresponding to about 10 percent to about 20 percent by weight of the 7β-epimer ester sulfoxide. Preferably about 15 percent by weight of DBU is used.

Suitable inert organic solvents which can be employed in the reaction are the halogenated hydrocarbon solvents such as methylene chloride, dichloroethane, trichloroethane, and like halogenated hydrocarbon solvents; and inert aprotic organic solvents such as acetonitrile, tetrahydrofuran, dioxane, and like aprotic solvents can be used. The reaction is carried out under substantially anhydrous conditions and, accordingly, the solvent used in the reaction is dried before use.

The preferred solvent in the epimerization process of this invention is methylene chloride, while the preferred temperature of the process is between about −5° C. and about 10° C.

The epimerization of the 7β-dimethylamidino 1α-oxide ester, when carried out according to the process of this invention, occurs rapidly at the low temperatures. In the following diagram, the epimerization at the 7-position is illustrated by partial structural formulas. In the formulas, the heavy spike indicates the β-configuration, while the dotted bonding lines indicate the α-configuration.

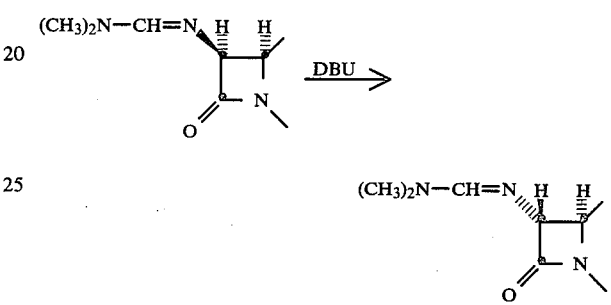

As defined above for the structural formula 1, R$_1$ can be a carboxy-protecting group. A wide variety of carboxy-protecting groups commonly used in the cephalosporin art for the temporary protection of the C$_4$ carboxy group are known. Preferable are the carboxy-protecting ester groups, for example, substituted alkyl esters, aryl methyl, and substituted aryl methyl esters. Examples of ester groups represented by the term R$_1$ in formula 1 are t-butyl, 2,2,2-trichloroethyl, 2,2,2-tribromoethyl, 2-iodoethyl, methoxymethyl, benzyl, p-nitrobenzyl, p-methoxybenzyl, diphenylmethyl, 4,4'-dimethoxydiphenylmethyl, phenacyl, p-chlorophenacyl, and like carboxy-protecting ester groups. The ester group R$_1$ functions to protect or block the acidic carboxylic acid group from untoward reactions or from participation in subsequent reactions used to convert the amidino intermediates to antibiotics.

Preferred ester groups represented by the term R$_1$ in the formula 1 are the p-nitrobenzyl, p-methoxybenzyl, and diphenylmethyl ester groups. An especially preferred ester group is the p-nitrobenzyl group. This ester function enhances the crystallinity of the amidino free base as well as the salts thereof.

As was mentioned above, the dimethylamidino compounds of the formula 1 are basic compounds which form acid addition salts with strong acids. For example, salts are formed with the mineral acids such as hydrochloric acid, hydrobromic acid, and sulfuric acid; and with the organic sulfonic acids such as benzenesulfonic acid, toluenesulfonic acid, p-chlorobenzenesulfonic acid, and p-bromobenzenesulfonic acid. The sulfonic acid addition salts are prepared with the free base by treating a solution of the free base in an organic solvent such as ethyl acetate with an aqueous solution of the acid. After stirring the mixed solutions, the organic layer is separated, dried, and concentrated to a small volume. Commonly, the salt crystallizes from the concentrate or, alternatively, it can be stirred with a solvent such as diethylether to cause precipitation of the salt. Alternatively, a solution of the free base in aqueous acetone on treatment with the sulfonic acid such as p-toluenesulfonic acid forms the corresponding sulfonate salt which commonly precipitates from solution.

The inorganic salts, eg. the hydrochloride, are obtained by extracting a solution of the free base in an organic solvent with dilute hydrochloric acid, eg. 1 N HCl. The aqueous phase is separated and concentrated to a small volume. The salt is precipitated by diluting the concentrate with acetone.

When in the process for preparing the compounds of the invention the 7-amino nucleus ester is reacted with phosphorus trichloride in DMF under Villsmeyer conditions, the hydrochloride salt of the dimethylamidino product is formed and can be isolated as such.

The compounds of the invention (formula 1) wherein R is hydrogen are converted by a sequence of reactions to 7-methoxy-3-methyl-1-oxa-β-lactam antibiotic compounds represented by the following structural formula.

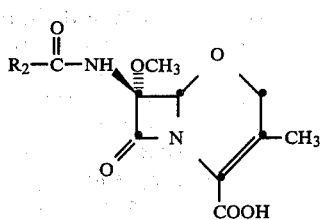

In the first step of the synthetic scheme, the compound of the formula 1 is treated with a mild acid to provide the corresponding 7α-formamido cephalosporin sulfoxide ester. The mild acid degradation is carried out according to the method described in copending application Ser. No. 183,918, filed Sept. 4, 1980, now U.S. Pat. No. 4,281,117 issued July 28, 1981. According to this method, the 7α-dimethylamidinocephalosporin ester 1α-oxide is treated in an inert organic solvent at a temperature between about 20° C. and about 45° C. with a carboxylic acid, a percarboxylic acid, or a phenol having a pH as measured in water of between about 2 and about 5 to provide the corresponding 7α-formamidocephalosporin ester sulfoxide. The mild acid degradation is illustrated in the following reaction scheme.

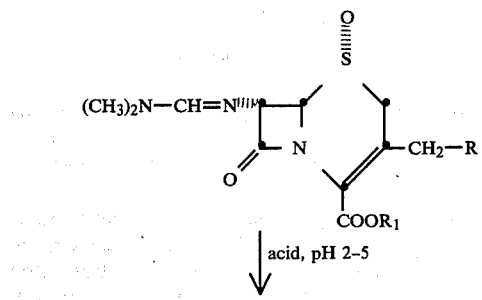

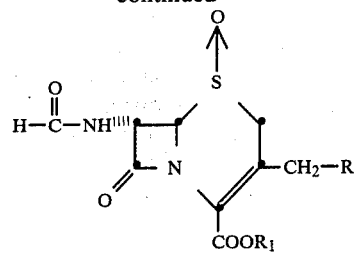

Examples of mild acids which can be used in the degradation include formic acid, acetic acid, propionic acid, benzoic acid, perbenzoic acid, m-chlorobenzoic acid, m-chloroperbenzoic acid, phenol, the cresols, p-chlorophenol, and like acids which have a pH as measured in water of between about 2 and about 5.

To illustrate the degradation reaction described above, p-nitrobenzyl 7α-[(dimethylaminomethylene)amino]-3-methyl-3-cephem-4-carboxylate 1α-oxide is reacted in acetone with 1.5 equivalents of m-chlorobenzoic acid with stirring at room temperature for about 14 hours. The reaction mixture was then evaporated to dryness under reduced pressure, and the residue of the crude product was taken up in a mixture of dilute hydrochloric acid and ethyl acetate. The organic layer is separated and while slurrying with water, the pH is adjusted to about 6.8. The organic layer is separated, dried, and evaporated to dryness under reduced pressure. The residue of purified product is obtained crystalline by trituration of the residue with petroleum ether or diethylether.

The 7α-formamidocephalosporin oxide ester is next converted to the corresponding 7α-aminocephalosporin ester oxide by hydrolysis with methanolic hydrochloric acid or with a Lewis acid under anhydrous conditions as described by British Patent Specification No. 1,321,265.

The 7α-amino cephalosporin ester sulfoxide is then acylated with a carboxylic acid to provide a 7α-acylamino cephalosporin ester sulfoxide, and the latter is reduced to the sulfide form. The acylation is carried out with a carboxylic acid such as to provide the desired side chain for the 1-oxa-β-lactam product. Representative side chains which can be incorporated on the 7α-amino nucleus sulfoxide are phenylacetyl, phenoxyacetyl, mandeloyl, thienylacetyl, furylacetyl, and like side chains. The acylation is carried out by reacting an active derivative of the desired carboxylic acid with the 7α-amino nucleus compound under the acylation conditions commonly employed for the acylation of other cephalosporin nucleus compounds. For example, the carboxylic acid can be converted to an acid halide or an acid azide for activation of the carboxy group in the acylation. Alternatively, the compound can be converted to a mixed anhydride or an active ester such as the hydroxybenzotriazol ester. In an example of the acylation, phenoxyacetyl chloride is reacted in acetone in the presence of sodium bicarbonate with p-nitrobenzyl 7α-amino-3-cephem-4-carboxylic acid sulfoxide to provide the corresponding 7-acylamino epimer, p-nitrobenzyl 7α-phenoxyacetylamino-3-methyl-3-cephem-4-carboxylate sulfoxide.

Following the acylation, the 7α-acyl ester sulfoxide is reduced to the sulfide form. The sulfoxide reduction is conveniently carried out with acetyl bromide in the presence of a bromine scavenger such as amylene according to the method described by Hatfield, U.S. Pat. No. 4,044,002.

The 7α-acylamino cephalosporin ester is then methoxylated in the 2-position of the cephem system. Stereochemically, the 2-alkoxylation proceeds to the 2α-alkoxy group, for example, the methoxy group. The alkoxylation reaction is illustrated by the following reaction scheme.

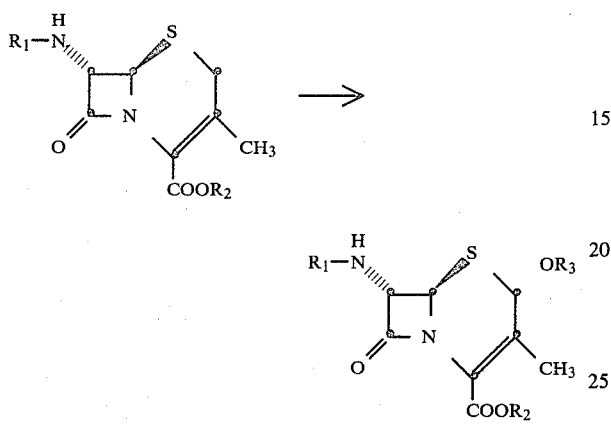

The 2α-alkoxylation reaction involved at this stage of the synthesis is analogous to procedures well known to those skilled in the art; see, for example, D. O. Spry, *Tetrahedron Letters*, 3717 (1972); A. Yoshida, S. Oida, and E. Ohki, *Chemical and Pharmaceutical Bulletin of Japan* (Tokyo), 23, 2507 and 2518 (1975); ibid., 24 362 (1976); ibid., 25, 2082 (1977); C. O. Kim and P. A. McGregor, *Tetrahedron Letters*, 409 (1978). Although the aforementioned references describe various methods of 2α-alkoxylation for 7β-isomers of cephalosporins, the preferred method for the conversion of 7α-acylamino-3-methyl-3-cephem-4-carboxylate to its corresponding 2α-alkoxy analog comprises the addition of N-chlorosuccinimide to a solution of the substrate cephem compound dissolved in a solvent mixture of an appropriate alcohol such as methyl alcohol and methylene chloride at room temperature. The desired 2α-alkoxy product can then be isolated by standard crystallization and chromatography techniques.

The 7α-acylamino-2α-alkoxy-3-methyl-3-cephem-4-carboxylic acid ester is then converted to a bisazetidinone disulfide dialdehyde and the latter is reduced to the corresponding dialcohol as described in copending applications Ser. Nos. 138,023, filed Apr. 7, 1980, now U.S. Pat. No. 4,293,495 issued Oct. 6, 1981, and 137,862 filed Apr. 7, 1980, now U.S. Pat. No. 4,293,493 issued Oct. 6, 1981. The reactions are shown in the following reaction scheme.

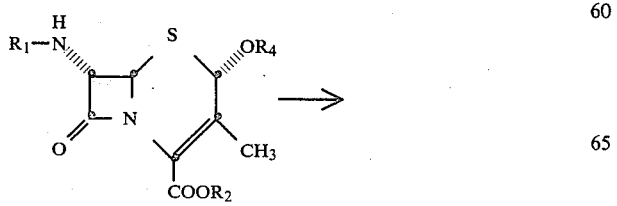

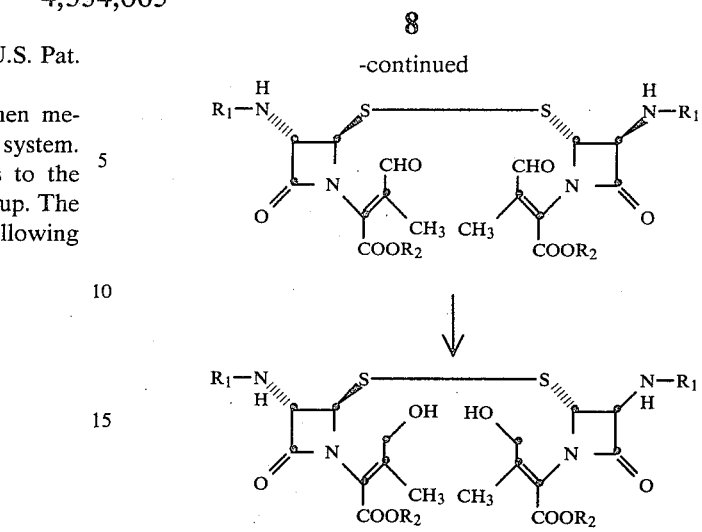

The preparation of the symmetrical disulfide dialdehyde of the above formula is carried out by reacting the 2α-alkoxy cephalosporin in an inert solvent such as methylene chloride with N-chlorosuccinimide at a temperature of about 0° C. The reaction mixture is then added to an aqueous suspension of mercury dichloride and cadmium carbonate at about room temperature to provide the disulfide dialdehyde of the above formula. The latter is recovered from the reaction mixture by conventional techniques, and the aldehyde groups thereof are reduced to provide the symmetrical disulfide dialcohol of the above formula.

The reduction of the dialdehyde is carried out with sodium cyanoborohydride by employing the method described by R. F. Borch, M. D. Bernstein, and H. Durat, *Journal of the American Chemical Society*, 93, 2897 (1971). According to this method, the symmetrical dialdehyde disulfide is dissolved in aqueous tetrahydrofuran and the pH of the solution is adjusted to about pH 3.5 by adding dilute sodium hydroxide. Sodium cyanoborohydride is then added in an amount in excess of 2 equivalents. The reaction mixture is stirred at room temperature for about 2 hours to provide the symmetrical disulfide dialcohol of the above formula. The alcohol can be purified by conventional extraction techniques.

The symmetrical azetidinone disulfide dialcohol is then cyclized to provide a 7α-acylamino 3-methyl-1-oxa-β-lactam compound represented by the following formula.

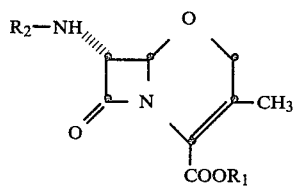

In the above formula, $R_2$ represents an acyl group derived from a carboxylic acid as described hereinabove, and $R_1$ is a carboxy-protecting group as defined above.

The formation of the 1-oxa-β-lactam compound is carried out by reacting the symmetrical azetidinone disulfide dialcohol with a cyclization reagent selected from the group consisting of a divalent mercury salt represented by the formula Hg(X)$_2$, wherein X is chloro, bromo, or trifluoroacetato, and a phosphine represented by the following formula (R$_4$)$_3$P, wherein R$_4$ is a lower alkyl, phenyl, or substituted phenyl.

When the cyclization is carried out in the presence of a divalent mercury compound, for example, mercury dichloride, the reaction is carried out in a dry, inert organic solvent such as acetonitrile. When, however, the reaction is carried out in the presence of a phosphine reagent as defined above, the reaction is carried out in a halogenated hydrocarbon solvent under anhydrous conditions. A preferred halogenated hydrocarbon solvent is 1,2-dichloroethane.

The 1-oxa-β-lactam ester having the side chain in the α-configuration can then be methoxylated in the 7-position to provide the corresponding 7β-acylamino-7α-methoxy-1-oxa-β-lactam compound represented by the following structural formula.

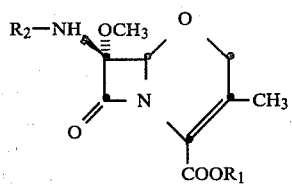

The methoxylation is carried out by reacting the 7α-acylamino-3-methyl 1-oxa β-lactam ester in an inert solvent at a temperature of about −70° C. with lithium methoxide and t-butyl hypochlorite. The reaction is carried out by adding the β-lactam starting material to a suspension of lithium methoxide in dry tetrahydrofuran in an inert atmosphere such as nitrogen or argon followed by the addition of the t-butyl hypochlorite. The reaction is carried out at a temperature of about −70° C. to about −25° C. Following completion the reaction is quenched by the addition of trimethylphosphite and glacial acetic acid. The 7α-methoxy-7β-acylamino product is recovered from the reaction mixture with conventional extraction techniques. As shown in the above structural formula for the methoxylation product, the 7-position side chain now has the 7β-configuration and the 7-position methoxy group has the α-configuration. This configuration of the products obtained with the compounds of the invention is the desired configuration for the known 1-oxa-β-lactam antibiotics.

Finally, the compounds of the above formula are deprotected to provide the free acids thereof. The antibiotic compounds obtained via this synthetic scheme are described in U.S. Pat. No. 4,226,866 and in Belgian Pat. No. 863,998.

The deesterification of the carboxy-protecting group is carried out by employing known deblocking procedures employed for the removal of these groups. For example, the preferred ester groups represented by R$_1$, the p-methoxybenzyl group, and the diphenylmethyl group are removed by treatment of the ester with trifluoroacetic acid in the presence of anisole at a temperature of about 15° C. to about 25° C. The preferred p-nitrobenzyl ester group can be removed by reductive deblocking techniques such as by catalytic hydrogenation over a hydrogenation catalyst such as palladium on carbon, or by chemical reduction with zinc dust and an acid such as acetic or formic acid. Other ester groups represented by the term R$_1$ are likewise removed by procedures known in the art.

While the above-described synthetic sequence describes the usefulness of the 7α-dimethylamidino compounds of the invention represented by the formula 1 wherein R is hydrogen, the intermediates represented by the formula 1 wherein R is acetoxy are useful in the preparation of the known 7β-acylamino-7α-methoxy-3-exomethylenecepham-4-carboxylic acids and esters represented by the following structural formula.

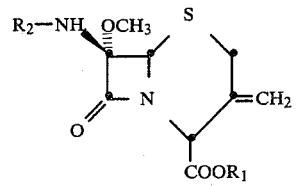

The 3-exomethylenecepham compounds are described by Hall, U.S. Pat. No. 4,042,472 and by Ponticello, U.S. Pat. No. 3,883,518.

The compounds of the invention represented by the formula 1 wherein R is acetoxy are converted to the 3-exomethylenecepham compounds by first converting the 7α-dimethylamidino cephalosporin ester sulfoxide to the 7α-amino nucleus sulfoxide ester via mild acid degradation of the 7α-dimethylamidino group to form the corresponding 7α-formamido ester sulfoxide. Hydrolysis of the latter with a Lewis acid in an anhydrous solvent, for example with phosphorus oxychloride in anhydrous methylene chloride provides the 7α-amino nucleus. Acylation of the 7α-amino sulfoxide ester provides the 7α-acylamino sulfoxide ester which on reduction of the sulfoxide to the sulfide forms the 7α-acylamino-3-acetoxymethyl-3-cephem-4-carboxylic acid ester. The preparation of the latter compound is carried out by following the same procedures as described hereinabove for the preparation of the corresponding 3-methyl-3-cephem compounds (formula 1, R=H).

The 7α-acylamino cephalosporin ester is then methoxylated in the 7-position to provide a 7β-acylamino-7α-methoxy-3-acetoxymethyl-3-cephem-4-carboxylic acid ester. The methoxylation reaction results in substitution of the methoxy group having the α-configuration, while the 7α-acylamino side chain is converted to the β-configuration. The 7α-methoxy compounds are then converted to the 3-exomethylenecepham compounds by the procedures described in U.S. Pat. Nos. 3,883,518 and 4,042,472.

The 7α[(dimethylaminomethylene)amino]-3-methyl- and 3-acetoxymethyl-3-cephem-4-carboxylic acid esters of the invention as represented by the structural formula 1 are thus useful intermediates in the correct epimeric form for conversion to 7α-methoxy-substituted cephalosporins and 1-oxa-β-lactam compounds as described above.

The following examples further illustrate the details and the manner by which the compounds of the invention are prepared.

EXAMPLE 1

7β-[(Dimethylaminomethylene)amino]cephalosporanic acid p-nitrobenzyl ester

To a solution of 3.2 g. (7.2 mmole) of 7-aminocephalosporanic acid p-nitrobenzyl ester in 22 ml. of dry dimethylformamide were added 2.0 g. (14.4 mmole) of phosphorus trichloride. The mixture was stirred at room temperature for about 16 hours and was poured into a mixture of ethyl acetate and an aqueous solution of 5% sodium bicarbonate saturated with sodium chloride. The organic layer was separated, washed with brine, dried over magnesium sulfate, and evaporated to dryness under vacuum. The product obtained as a crystalline residue was triturated with diethyl ether. There were obtained 2.8 g. (84% yield) of the title compound.

The following data were obtained with the product.

Elemental analysis calculated for $C_{20}H_{22}N_4O_7S$: Theory: C, 51.94; H, 4.80; N, 12.11. Found: C, 51.65; H, 4.83; N, 11.91.

NMR (T60 MHz, $CHCl_3$): 7.95 (s, 3H, acetoxy methyl), 7.09 (s, 6H, $N(CH_3)_2$), 6.54 (ABq, 2H, $C_2$—$H_2$), 5.40-4.79 (2 doublets and Abq, 4H, $C_7$—H, $C_6$—H and $C_3$—$CH_2$), 4.66 (s, 2H, ester $CH_2$), 2.50-1.77 (2 doublets, 4H, aromatic-H) and 2.50 (s, 1H, CH)tau.

IR ($CHCl_3$): carbonyl absorption bands at 1780 $cm^{-1}$ and 1738 $cm^{-1}$.

UV ($CH_3CN$): λ max 260 mμ ($\epsilon$ = 18,262).

Electrometric titration (66% DMF): pKa 6.95; apparent molecular weight 487 (calculated MW 463).

EXAMPLE 2

7β-[(Dimethylaminomethylene)amino]cephalosporanic acid p-nitrobenzyl ester, p-toluenesulfonic acid salt p-Nitrobenzyl 7β-[(dimethylaminomethylene)amino]cephalosporanate, 2.0 g. (4.3 mmole) prepared as described by Example 1, was dissolved in 130 ml. of ethyl acetate and the solution was filtered. To the filtrate was added a solution of 860 mg. of p-toluenesulfonic acid (4.5 mmole) in 35 ml. of ethyl acetate. An immediate crystalline precipitate of the title salt was formed and was collected by filtration. There were obtained 2.6 g. (95% yield) of the tosylate salt.

The following data were obtained with the salt.

Elemental analysis calculated for $C_{27}H_{30}N_4O_{10}S_2$: Theory: C, 51.10; H, 4.76; N, 8.83. Found: C, 51.25; H, 4.76; N, 8.73.

NMR (T60 MHz, $DMSOd_6$): 7.96 (s, 3H, acetoxy methyl), 7.70 (s, 3H, tosyl methyl), 6.81 (d, 6H, $N(CH_3)_2$) 6.26 (s, 2H, $C_2$—$H_2$), 5.10 (ABq, 2H, $C_3$—$CH_2$), 4.75 (s, 1H, $C_6$—H), 4.55 (s, 2H, ester-$CH_2$), 4.21 (d, 1H, $C_7$—H), 2.96-1.70 (4 doublets, 8H, aromatic-H) and 1.70 (s, 1H, CH)tau.

IR (mull): carbonyl absorption bands at $1790^{cm-1}$, $1745^{cm-1}$ and $1713^{cm-1}$.

UV ($CH_3CN$) λ max 262 mμ ($\epsilon$ = 18,900).

EXAMPLE 3

7β-[(Dimethylaminomethylene)amino]cephalosporanic acid p-nitrobenzyl ester, 1α-oxide To a solution of 2.9 g. (4.6 mmole) of 7β-[(dimethylaminomethylene)amino]cephalosporanic acid p-nitrobenzyl ester p-toluenesulfonate in 135 ml. of acetone and 22 ml. of water were added at room temperature with stirring 980 mg. (4.8 mmole) of m-chloroperbenzoic acid (85% pure). The reaction was stirred at room temperature for 1.5 hours after which the acetone was evaporated from the mixture in vacuo. The aqueous residue was extracted with ethyl acetate to remove excess peracid. The aqueous phase was then slurried with ethyl acetate and the pH of the slurry was adjusted to pH 7.5 with 1 N sodium hydroxide. The ethyl acetate layer was separated, washed with water, dried over magnesium sulfate and concentrated in vacuo to a volume of about 70 ml. The title compound, 1.3 g. (58 percent yield) crystallized from the concentrate, was filtered and dried.

The following analytical data were obtained with the crystalline 1α-oxide ester product.

Elemental analysis calculated for $C_{20}H_{22}N_4O_8S$: Theory: C, 50.20; H, 4.63; N, 11.71. Found: C, 49.92; H, 4.50; N, 11.45.

IR (mull): carbonyl absorption bands at 1771, 1730 and $1720^{cm-1}$.

UV (acetonitrile) λ max 268 mμ ($\epsilon$ = 17,427).

NMR (100 MHz, $DMSOd_6$) tau 7.98 (s, 3H, acetoxy—$CH_3$), 7.19 (s, 6H, N—$(CH_3)_2$), 6.33 (ABq, 2H, $C_2$—$H_2$), 5.21 (d, 1H, $C_6$—H), 5.12 (ABq, 2H, $C_3$—$CH_2$), 4.72 (d, 1H, $C_7$—H), 4.55 (s, 2H, ester—$CH_2$), 2.44 (s, 1H, CH) and 2.32-1.71 (2d, 4H, aromatic H).

EXAMPLE 4

7α-[(Dimethylaminomethylene)amino]cephalosporanic acid p-nitrobenzyl ester, 1α-oxide A solution of 479 mg. (1 mmole) of 7β-[(dimethylaminomethylene)amino]cephalosporanic acid p-nitrobenzyl ester, 1α-oxide in 8 ml. of dry methylene chloride was cooled in an ice-water bath and 23 mg. (0.15 mmole) of 1,5-diazabicyclo[5.4.0]undec-5-ene were added. The epimerization mixture was stirred for 30 minutes in the cold and was then warmed to room temperature for 4.5 hours. The reaction mixture was poured into a mixture of ethyl acetate and 30 ml. of pH 7 (0.05 M) buffer. The organic phase was separated, added to water and the pH acidified to pH 2.5 with 1 N hydrochloric acid. The acidic aqueous layer was separated, slurried with ethyl acetate and the pH of the slurry adjusted to 7 with 1 N sodium hydroxide. The ethyl acetate phase was separated, washed with water, dried over magnesium sulfate and evaporated to dryness in vacuo to yield the product. The product was triturated with diethyl ether before analysis.

The following analytical data were obtained with the 7α,1α-oxide ester epimer.

Elemental analysis calculated for $C_{20}H_{22}N_4O_8S$: Theory: C, 50.20; H, 4.63; N, 11.71. Found: C, 50.22; H, 4.69; N, 11.50.

NMR (T60 MHz, $CDCl_3$) tau 7.92 (s, 3H, acetoxy—$CH_3$), 7.10 (s, 6H, N—$(CH_3)_2$), 6.41 (ABq, 2H, $C_2$—$H_2$), 5.61 (d, 1H, $C_6$—H), 5.08 (ABq, 2H, $C_3$—$CH_2$), 5.00 (d, 1H, $C_7$—H), 4.57 (s, 2H, ester $CH_2$), 2.50 (s, 1H, CH), and 2.4-1.7 (2d, 4H, aromatic H).

EXAMPLE 5

7α-[(Dimethylaminomethylene)amino]cephalosporanic acid p-nitrobenzyl ester, 1α-oxide p-toluenesulfonate A solution of 340 mg. (0.5 mmole) of 7β-[(dimethylaminomethylene)amino]cephalosporanic acid p-nitrobenzyl ester, 1α-oxide in 4 ml. of dry methylene chloride was cooled in an ice-water bath and a solution of 12 mg. (0.08 mmole) of dry DBU in 1 ml. of dry methylene chloride was added to the cold solution. The epimerization mixture was stirred in the cold for 45 minutes and then at room temperature for 1 hour.

The reaction mixture was added slowly to a mixture of 122 mg. (0.64 mmole) of p-toluenesulfonic acid in 10 ml. of water and 100 ml. of ethyl acetate. After addition was complete the ethyl acetate layer was separated, washed with 2 ml. of water, dried over magnesium sulfate and concentrated in vacuo in a room temperature water bath to a volume of about 4 ml. The title compound, 170 mg. (52 percent yield), crystallized from the concentrate and was filtered and dried.

The following analytical data were obtained with the crystalline 7α,1α-oxide ester epimer salt.

Elemental analysis calculated for $C_{27}H_{30}N_4O_{11}S_2$: Theory: C, 49.84; H, 4.65; N, 8.61. Found: C, 48.39; H, 4.41; N, 7.88.

IR (Nujol mull): carbonyl absorption bands at 1788, 1750, 1740, 1720 and 1700 $cm^{-1}$.

UV (acetonitrile) λ max 270 mμ (ε=18,850).

Electrometric titration (66% dimethylformamide): pKa's at 6.87 and 12.9.

EXAMPLE 6 p-Nitrobenzyl-7β-[(dimethylaminomethylene)amino]-3-methyl-3-cephem-4-carboxylate hydrochloride salt To a solution of 26 g. (50 mmole) of p-nitrobenzyl 7-amino-3-cephem-4-carboxylate hydrochloride in 150 ml. of dry DMF were added with stirring at room temperature 14.1 g. (102 mmoles, 9.0 ml.) of phosphorus trichloride. The reaction mixture was stirred for 5 hours at room temperature. A crystalline precipitate of the product formed with the first hour. The product was filtered and washed with DMF and then with diethyl ether. There were obtained 12.7 g. (58% yield) of the title compound.

The following data were obtained for the crystalline product.

NMR (T60 MHz, DMSOd$_6$): signals (tau) at 7.81 (s, 3H, C$_3$—CH$_3$), 6.71 (d, 6H, N—(CH$_3$)$_2$), 6.28 (s, 2H, C$_2$—H$_2$), 4.76 (d, 1H, C$_6$—H), 4.58 (s, 3H, ester CH$_2$), 4.22 (d, 1H, C$_7$—H), 2.37–1.68 (2d, 4H, aromatic H), and 1.51 (s, 1H, CH).

Elemental analysis calculated for $C_{18}H_{21}N_4O_5SCl$: Theory: C, 49.03; H, 4.80; N, 12.71. Found: C, 48.80; H, 4.90; N, 12.06.

EXAMPLE 7 p-Nitrobenzyl 7β-[(dimethylaminomethylene)amino]-3-methyl-3-cephem-4-carboxylate free base

Method A

A suspension of 6.5 g. (18.6 mmole) of p-nitrobenzyl 7-amino-3-methyl-3-cephem-4-carboxylate in 100 ml. of dimethylformamide dimethyl acetal acetate was stirred for about 16 hours at room temperature. The reaction mixture was dispersed in a mixture of ice water and ethyl acetate and the organic phase was separated, washed with brine, dried over magnesium sulfate and evaporated to dryness in vacuo. The residue of the title compound obtained was crystalline and was triturated with diethyl ether and filtered. There were obtained 3.2 g. (43% yield).

Method B

To a suspension of 3.9 g. (10 mmole) of p-nitrobenzyl 7-amino-3-methyl-3-cephem-4-carboxylate hydrochloride in 130 ml. of DMF containing 1 ml. of water were added 8.8 g. (64 mmole, 5.6 ml.) of phosphorus trichloride and the mixture was stirred for 4 hours at room temperature. The reaction mixture was added to a mixture of a 5% aqueous solution of sodium bicarbonate and ethyl acetate and the mixture shaken. The organic phase was separated, washed several times with brine, dried over magnesium sulfate and evaporated to dryness in vacuo. The residue of product was crystalline and after trituration with diethyl ether a 75% yield of the title compound was obtained. The following data were obtained for the crystalline product.

NMR (T60 MHz, CDCl$_3$) signals (tau) at 7.89 (s, 3H, C$_3$—CH$_3$), 7.10 (s, 6H, N(CH$_3$)$_2$), 6.62 (ABq, 2H, C$_2$—H$_2$), 5.02 (d, 1H, C$_6$—H), 4.86 (d, 1H, C$_7$—H), 2.45–1.72 (2d, 4H, aromatic H), and 2.45 (s, 1H, CH).

Elemental analysis calculated for $C_{18}H_{20}N_4O_5S$: Theory: C, 53.46; H, 4.98; N, 13.85. Found: C, 52.57; H, 4.85; N, 13.06.

EXAMPLE 8 p-Nitrobenzyl 7β-[(dimethylaminomethylene)amino]-3-methyl-3-cephem-4-carboxylate 1α-sulfoxide To a solution of 8.8 g. (20 mmole) of p-nitrobenzyl 7β-[(dimethylaminomethylene)amino]-3-methyl-3-cephem-4-carboxylate in 100 ml. of water and 160 ml. of acetone were added 4.2 g. (21 mmole) of m-chloroperbenzoic acid and the reaction mixture was stirred at room temperature for 1.5 hours. The reaction mixture was evaporated in vacuo to remove the acetone and the aqueous concentrate was slurried in ethyl acetate. The pH of the slurry was adjusted to 7.8 with 1 N sodium hydroxide and the organic phase was separated, washed with water, dried over magnesium sulfate and concentrated to a small volume in vacuo. The concentrate was diluted with diethyl ether and 6.9 g. (82%) of the α-sulfoxide crystallized from the diluted concentrate.

The following data were obtained for the product.

NMR (T60 MHz, CDCl$_3$): signals (tau) at 7.63 (s, 3H, C$_3$—CH$_3$), 7.10 (s, 6H, N(CH$_3$)$_2$) 6.60 (ABq, 2H, C$_2$—H$_2$), 5.59 (d, 1H, C$_6$—H), 4.75 (d, 1H, C$_7$—H), 4.61 (s, 2H, ester CH$_2$), 2.45–1.70 (2d, 4H, aromatic H), and 2.30 (s, 1H, CH).

Elemental analysis calculated for $C_{18}H_{20}N_4O_6S$: Theory: C, 51.42; H, 4.77; N, 13.33. Found: C, 51.17; H, 4.50; H, 13.20.

EXAMPLE 9 p-Nitrobenzyl 7α-[(dimethylaminomethylene)amino]-3-methyl-3-cephem-4-carboxylate 1α-sulfoxide p-toluenesulfonate salt To a solution of 420 mg. (1 mmole) of p-nitrobenzyl 7β-[(dimethylaminomethylene)amino]-3-methyl-3-cephem-4-carboxylate 1α-sulfoxide in 8 ml. of dry methylene chloride cooled in an ice-water bath were added 23 mg. (0.15 mmole) of dry DBU. The mixture was stirred in the cold for 45 minutes and then at about room temperature for 3.5 hours. After this time, a thin layer chromatogram run on the reaction mixture showed the reaction was incomplete. An additional 23 mg. of DBU were added and the mixture was stirred at room temperature for 1.5 hours longer.

The reaction mixture was slowly added to a stirred solution of 380 mg. (2 mmole) of p-toluenesulfonic acid in 20 ml. of water and 100 ml. of ethyl acetate. The organic layer was separated, washed with water, dried and evaporated to near dryness in vacuo. The residue was layered with diethyl ether and the 7α-epimeric product crystallized and was filtered. There were obtained 250 mg. of the crystalline title compound (43% yield). The following data for the crystalline product were obtained.

NMR (T60 MHz, DMSOd6): signals (tau) at 7.97 (s, 3H, C3—CH3), 7.68 (s, 3H, p—CH3), 6.89 and 6.70 (2s, 6H, N(CH3)2), 6.12 (s, 2H, C2—H2), 4.91 (d, 1H, C6—H), 4.74 (d, 1H, C7—H), 4.51 (s, 2H, ester CH2), 2.90–1.66 (4d, 8H, aromatic H) and 1.32 (s, 1H, CH).

Elemental analysis calculated for $C_{25}H_{28}N_4O_9S$: Theory: C, 50.67; H, 4.76; N, 9.45. Found: C, 50.47; H, 4.98; N, 9.26.

I claim:

1. A compound of the formula

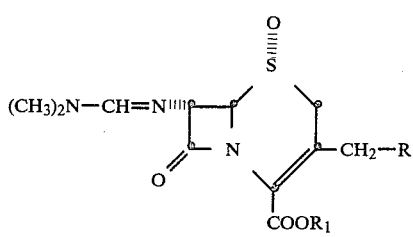

wherein R is hydrogen or acetoxy; $R_1$ is a carboxy protecting group; and the acid addition salts thereof.

2. The compound of claim 1 wherein R is hydrogen.

3. The compound of claim 2, said compound being p-nitrobenzyl 7α-[(dimethylaminomethylene)amino]-3-methyl-3-cephem-4-carboxylate 1α-oxide.

4. An acid addition salt of the compound of claim 2.

5. The salt of claim 4, said salt being p-nitrobenzyl 7α-[(dimethylaminomethylene)amino]-3-methyl-3-cephem-4-carboxylate 1α-oxide, p-toluenesulfonate.

6. The compound of claim 1 wherein R is acetoxy.

7. The compound of claim 6, said compound being p-nitrobenzyl 7α-[(dimethylaminomethylene)amino]-3-acetoxymethyl-3-cephem-4-carboxylate 1α-oxide.

8. An acid addition salt of the compound of claim 6.

9. The salt of claim 8, said salt being p-nitrobenzyl 7α-[(dimethylaminomethylene)amino]-3-acetoxymethyl-3-cephem-4-carboxylate 1α-oxide, p-toluenesulfonate.

10. A process for preparing the compound of claim 1 which comprises treating in an inert organic solvent at a temperature between about −10° C. and about 25° C. a 7β-(dimethylamidino)-3-cephem ester 1α-oxide of the formula

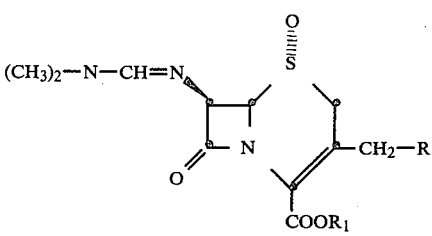

wherein R is hydrogen or acetoxy, and $R_1$ is a carboxy protecting group, with 1,5-diazabicyclo[5.4.0]undec-5-ene in an amount corresponding to between about 10 percent and about 25 percent by weight of said 7β-(dimethylamidino)-3-cephem ester 1α-oxide.

11. The process of claim 10 wherein R is hydrogen.

12. The process of claim 10 wherein R is acetoxy.

13. The process of claim 10 wherein the 1,5-diazabicyclo[5.4.0]undec-5-ene is used in an amount corresponding to about 15 percent by weight of the 7β-(dimethylamidino)-3-cephem ester 1α-oxide.

* * * * *